United States Patent
Chen et al.

(10) Patent No.: US 11,708,379 B2
(45) Date of Patent: Jul. 25, 2023

(54) MECHANOCHEMICAL SYNTHESIS OF METAL-ORGANIC FRAMEWORKS FOR MOLECULAR SIEVING AND COMPOSITIONS AND METHODS OF USE THEREOF

(71) Applicant: The Board of Regents of The University of Texas System, Austin, TX (US)

(72) Inventors: Banglin Chen, San Antonio, TX (US); Rui-Biao Lin, San Antonio, TX (US); Yanshu Shi, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 180 days.

(21) Appl. No.: 17/200,108

(22) Filed: Mar. 12, 2021

(65) Prior Publication Data
US 2021/0284661 A1     Sep. 16, 2021

Related U.S. Application Data

(60) Provisional application No. 62/988,854, filed on Mar. 12, 2020.

(51) Int. Cl.
*B01D 53/04*     (2006.01)
*C07F 3/00*     (2006.01)

(52) U.S. Cl.
CPC .............. *C07F 3/003* (2013.01); *B01D 53/04* (2013.01); *B01D 2253/204* (2013.01); *B01D 2256/24* (2013.01); *B01D 2257/7022* (2013.01)

(58) Field of Classification Search
CPC ... B01J 20/226; B01J 20/28061; B01D 53/02; B01D 53/04; B01D 2253/204;
(Continued)

(56) References Cited

U.S. PATENT DOCUMENTS

2022/0266219 A1*    8/2022    Abney ...................... C07F 3/02

FOREIGN PATENT DOCUMENTS

WO     WO 2019/183635       9/2019

OTHER PUBLICATIONS

Aguado et al., "Absolute Molecular Sieve Separation of Ethylene/Ethane Mixtures With Silver Zeolite A." *J. Am. Chem. Soc.*, 134:14635-14637, 2012.
(Continued)

*Primary Examiner* — Sharon Pregler
(74) *Attorney, Agent, or Firm* — Parker Highlander PLLC

(57) ABSTRACT

Methods of preparing and using a metal-organic framework (MOF) are provided herein, including methods of using an MOF comprising a repeat unit of the formula $[ML]_n$, wherein M is a divalent metal ion and L is a ligand of the formula:

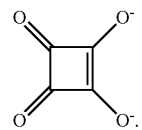

The MOFs provided herein may be used in the separation of two or more molecules from each other. In some embodiments, the molecules are ethylene and ethane. In some embodiments, UTSA-280 may be synthesized from calcium oxide (CaO) or calcium hydroxide $(Ca(OH)_2)$ and squaric acid (SA) through mechanochemical synthesis.

20 Claims, 13 Drawing Sheets
(5 of 13 Drawing Sheet(s) Filed in Color)

CaO
+

Squaric Acid

Mechanochemical Synthesis →

(58) Field of Classification Search
CPC ...... B01D 2257/102; B01D 2257/7022; B01D 2257/504; B01D 2256/24; C07C 7/13; C07C 9/06; C07C 11/02; C07F 3/003; Y02C 20/40; Y02P 20/151
See application file for complete search history.

(56) References Cited

OTHER PUBLICATIONS

Anson et al., "Adsorption of Ethane and Ethylene on Modified ETS-10." Chem. Eng. Sci., 63:4171-4175, 2008.
Bachman et al. "$M_2$(m-dobdc) (M=Mn, Fe, Co, Ni) Metal-Organic Frameworks as Highly Selective, High-Capacity Adsorbents for Olefin/Paraffin Separations." J. Am. Chem. Soc., 139:15363-15370, 2017.
Bao et al., "Molecular Sieving of Ethane from Ethylene through the Molecular Cross-Section Size Differentiation in Gallate-based Metal—Organic Frameworks." Angew. Chem. Int. Ed., 130(49):16252-57, 2018.
Bao et al., "Potential of Microporous Metal—Organic Frameworks for Separation of Hydrocarbon Mixtures." Energy Environ. Sci., 9:3612-3641, 2016.
Barone et al., "Role and Effective Treatment of Dispersive Forces in Materials: Polyethylene and Graphite Crystals as Test Cases." J. Comput. Chem. 30(6): 934-939, 2009.
Bereciartua et al., "Control of Zeolite Framework Flexibility and Pore Topology for Separation of Ethane and Ethylene." Science, 358:1068-1071, 2017.
Bloch et al., "Hydrocarbon Separations in a Metal-Organic Framework with Open Iron(II) Coordination Sites." Science, 335:1606-1610, 2012.
Cadiau et al., "A metal-organic framework—based splitter for separating propylene from propane." Science, 353:137-140, 2016.
Chang et al., "Immobilization of Ag(i) into a metal-organic framework with -SO3H sites for highly selective olefin-paraffin separation at room temperature." Chem. Commun. 51:2859-2862, 2015.
Chu et al., "The Path Towards Sustainable Energy." Nat. Mater., 16:16-22, 2017.
Crawford et al., "Synthesis by extrusion: continuous, large-scale preparation of MOFs using little or no solvent." Chem. Sci., 6(3):1645-49, 2015.
Cui et al., "A microporous metal-organic framework of sql topology for $C_2H_2/CO_2$ separation." Inorganica Chimica Acta, 495:118938, 2019.
Cui et al., "Pore chemistry and size control in hybrid porous materials for acetylene capture from ethylene." Science, 353:141-144, 2016.
Faiz et al., "ChemInform Abstract: Olefin/Paraffin Separation Using Membrane Based Facilitated Transport/Chemical Absorption Techniques." Chem. Eng. Sci., 73:261-284, 2012.
Friščić et al., "Ion- and Liquid-Assisted Grinding: Improved Mechanochemical Synthesis of Metal—Organic Frameworks Reveals Salt Inclusion and Anion Templating." Angew. Chem. Int. Ed., 49(4):712-15, 2010.
Furukawa et al., "The Chemistry and Applications of Metal-Organic Frameworks." Science 341(6149):1230444, 2013.
Geier et al., "Selective Adsorption of Ethylene over Ethane and Propylene over Propane in the Metal—Organic Frameworks $M_2$(dobdc) (M=Mg, Mn, Fe, Co, Ni, Zn)." Chem. Sci. 4:2054-2061, 2013.
Giannozzi et al., "Quantum Espresso: a Modular and Open-Source Software Project for Quantum Simulations of Materials." J. Phys.: Condens. Matter 21:395502, 2009.
He et al., "Metal—Organic Frameworks with Potential for Energy-Efficient Adsorptive Separation of Light Hydrocarbons." Energy Environ. Sci. 5:9107-9120, 2012.
Horike et al., "Postsynthesis Modification of a Porous Coordination Polymer by Licl to Enhance H+ Transport." J. Am. Chem. Soc., 135:4612-4615, 2013.

Ji et al., "Transformation of Metal—Organic Framework Secondary Building Units into Hexanuclear Zr-Alkyl Catalysts for Ethylene Polymerization." J. Am. Chem. Soc., 139:11325-11328, 2017.
Julien et al., "In Situ Monitoring and Mechanism of the Mechanochemical Formation of a Microporous MOF-74 Framework." J. Am. Chem. Soc., 138(9):2929-32, 2016.
Julien et al., "Metal—Organic Frameworks Meet Scalable and Sustainable Synthesis." Green Chemistry, 19(12):2729-47, 2017.
Kishida et al., "Recognition of 1,3-Butadiene by a Porous Coordination Polymer." Angew. Chem. Int. Ed. 55:13784-13788, 2016).
Kitagawa, "Porous Materials and the Age of Gas." Angew. Chem. Int. Ed., 54:10686-10687, 2015.
Klet et al., "Single-Site Organozirconium Catalyst Embedded in a Metal—Organic Framework." J. Am. Chem. Soc. 137:15680-15683, 2015.
Krishna et al. "The Maxwell-Stefan Description of Mixture Diffusion in Nanoporous Crystalline Materials." Microporous Mesoporous Mater. 185:30-50, 2014.
Li et al., "A Metal—Organic Framework with Suitable Pore Size and Specific Functional Sites for the Removal of Trace Propyne from Propylene." Angew. Chem. Int. Ed., 130(46): 15403-08, 2018.
Li et al., "Ethane/Ethylene Separation in a Metal-Organic Framework with Iron-Peroxo Sites." Science, 362(6413):443-46, 2018.
Li et al., "Introduction of Π-Complexation into Porous Aromatic Framework for Highly Selective Adsorption of Ethylene over Ethane." J. Am. Chem. Soc., 136:8654-8660, 2014.
Li et al., "Selective Gas Adsorption and Separation in Metal—Organic Frameworks." Chem. Soc. Rev., 38(5):1477-1504, 2009.
Li et al., "The Metal-Organic Framework MIL-53(Al) Constructed from Multiple Metal Sources: Alumina, Aluminum Hydroxide, and Boehmite." Chemistry—A European Journal, 21(18):6913-20, 2015.
Liao et al., "Controlling Guest Conformation for Efficient Purification of Butadiene." Science, 356:1193-1196, 2017.
Lin et al., "Boosting Ethane/Ethylene Separation within Isoreticular Ultramicroporous Metal-Organic Frameworks." J. Am. Chem. Soc., 140(40): 12940-46, 2018.
Lin et al., "Exploration of Porous Metal—Organic Frameworks for Gas Separation and Purification." Coord. Chem. Rev., 378:87-103, 2019.
Lin et al., "Microporous Metal-Organic Framework Materials for Gas Separation." Chem, 6(2):337-63, 2020.
Lin et al., "Molecular Sieving of Ethylene from Ethane Using a Rigid Metal—Organic Framework." Nat. Mater., 17(12):1128, 2018.
Lin et al., "Optimized Separation of Acetylene from Carbon Dioxide and Ethylene in a Microporous Material." J. Am. Chem. Soc., 139(23):8022-28, 2017.
Lin et al., "Our Journey of Developing Multifunctional Metal-Organic Frameworks." Coord. Chem. Rev., 384:21-36, 2019.
Lin et al., "Solvent/Additive-Free Synthesis of Porous/Zeolitic Metal Azolate Frameworks from Metal Oxide/Hydroxide." Chem. Commun., 47(32):9185-87, 2011.
Lin, "Molecular Sieves for Gas Separation" Science, 353:121-122, 2016.
Liu et al., "The Geometry of Periodic Knots, Polycatenanes and Weaving from a Chemical Perspective: a Library For Reticular Chemistry." Chem. Soc. Rev., 47(12):4642-64, 2018.
Ma et al., "Preparation and Gas Adsorption Studies of Three Mesh-Adjustable Molecular Sieves With a Common Structure." J. Am. Chem. Soc., 131:6445-6451, 2009.
Ma et al., "Zeolitic Imidazolate Framework Membranes Made by Ligand-Induced Permselectivation." Science, 361(6406):1008-11, 2018.
Majano et al., "Scalable Room-Temperature Conversion of Copper(II) Hydroxide into HKUST-1 ($Cu_3(btc)_2$)." Adv. Mater., 25(7):1052-57, 2013.
Maserati et al., "Minute-MOFs: Ultrafast Synthesis of M2(dobpdc) Metal—Organic Frameworks from Divalent Metal Oxide Colloidal Nanocrystals." Chem. Mater., 28(5):1581-88, 2016.
Mofarahi et al., "Pure and binary adsorption isotherms of ethylene and ethane on zeolite 5A." Adsorption, 19:101-110, 2013.
Nugent et al., "Porous Materials with Optimal Adsorption Thermodynamics and Kinetics for CO2 Separation." Nature, 495:80-84, 2013.

(56) References Cited

OTHER PUBLICATIONS

Pan et al., "Separation of Hydrocarbons with a Microporous Metal—Organic Framework." *Angew. Chem. Int. Ed.*, 45:616-619, 2006.
Peng et al., "Membranes. Metal-Organic Framework Nanosheets as Building Blocks for Molecular Sieving Membranes." *Science*, 346:1356-1359, 2014.
Robl et al., "Alkaline-earth squarates III.$CaC_4O_4 \cdot 2.5H_2O$, a novel polymer complex with zeolitic properties (1)." *Mater. Res. Bull.*, 22:373-380, 1987.
Rubio-Martinez et al., "New Synthetic Routes Towards MOF Production at Scale." *Chem. Soc. Rev.*, 46(11):3453-80, 2017.
Sen et al., "Cooperative Bond Scission in a Soft Porous Crystal Enables Discriminatory Gate Opening for Ethylene over Ethane." *J. Am. Chem. Soc.*, 139:18313-18321, 2017.
Shi et al., "Structure Directing Agents Induced Morphology Evolution and Phase Transition From Indium-Based Rho- to Sod-ZMOF." *CrystEngComm*, 19(30):4265-68, 2017.
Sholl et al., "Seven Chemical Separations to Change the World." *Nature*, 532:435-437, 2016.
Stojaković et al., "Vortex Grinding for Mechanochemistry: Application for Automated Supramolecular Catalysis and Preparation of a Metal-Organic Framework." *Chem. Commun.*, 48(64):7958-60, 2012.
Vaidhyanathan et al., "Direct Observation and Quantification of $CO_2$ Binding Within an Amine-Functionalized Nanoporous Solid." *Science*, 330:650-653, 2010.
Webster et al., "Molecular Dimensions for Adsorptives." *J. Am. Chem. Soc.*, 120:5509-5516, 1998.
Yang et al., "Supramolecular Binding and Separation of Hydrocarbons Within a Functionalized Porous Metal—Organic Framework." *Nat. Chem.* 7:121-129, 2014. With Supplemental Information.
Yang, "Adsorbents: Fundamentals and Applications." (John Wiley & Sons, Inc.), 280-381, 2003.
Yoon et al., "Controlled Reducibility of a Metal-Organic Framework With Coordinatively Unsaturated Sites for Preferential Gas Sorption." *Angew. Chem. Int. Ed.*, 49:5949-5952, 2010.
Yoon et al., "Selective Nitrogen Capture by Porous Hybrid Materials Containing Accessible Transition Metal Ion Sites." *Nat. Mater.*, 16:526-531, 2016.
Yuan et al., "High Reactivity of Metal-Organic Frameworks Under Grinding Conditions: Parallels with Organic Molecular Materials." *Angew. Chem. Int. Ed.*, 49(23):3916-19, 2010.
Yuan et al., "Study of the Mechanochemical Formation and Resulting Properties of an Archetypal MOF: $Cu_3(BTC)_2$ (BTC=1,3,5-benzenetricarboxylate)." *CrystEngComm*, 12(12):4063-65, 2010.
Zhai et al., "An Ultra-Tunable Platform for Molecular Engineering of High-Performance Crystalline Porous Materials." *Nat. Commun.*, 7:13645, 2016.
Zhang et al., "Highly Selective Adsorption of Ethylene Over Ethane in a MOF Featuring the Combination of Open Metal Site and Π-Complexation." *Chem. Commun.* 51:2714-2717, 2015.
Zhang, et al., "Cracking of Simulated Oil Refinery off-Gas over a Coal Char, Petroleum Coke, and Quartz." *Energy & Fuels*, 22:1142-1147, 2008.
Zhao et al., "Facile Conversion of Hydroxy Double Salts to Metal-Organic Frameworks Using Metal Oxide Particles and Atomic Layer Deposition Thin-Film Templates." *J. Am. Chem. Soc.*, 137(43):13756-59, 2015.
Zheng et al., "MOF-808: a Metal-Organic Framework with Intrinsic Peroxidase-Like Catalytic Activity at Neutral pH for Colorimetric Biosensing." *Inorg. Chem.*, 57:9096, 2018.

\* cited by examiner

MECHANOCHEMICAL SYNTHESIS OF METAL-ORGANIC FRAMEWORKS FOR MOLECULAR SIEVING AND COMPOSITIONS AND METHODS OF USE THEREOF

REFERENCE TO RELATED APPLICATIONS

This application claims the benefit of priority to U.S. Provisional Application No. 62/988,854, filed on Mar. 12, 2020, the entire content of which is hereby incorporated by reference.

BACKGROUND

I. Field

The present disclosure relates generally to the fields of chemistry and materials science. More particularly, it concerns metal-organic frameworks, methods of preparation thereof, compositions thereof and methods of use thereof, including separating gas molecules such as ethylene and ethane.

II. Description of Related Art

Metal-organic frameworks (MOFs) are porous solids that can be straightforwardly assembled from the combinations of various metal ions/clusters and organic linkers, showing exceptional porosity, high modularity and diverse functionality (Furukawa et al., Science 341(6149):1230444, 2013.; Liu et al., Chem. Soc. Rev., 47(12):4642-64, 2018; Lin et al., Chem, 6(2):337-63, 2020).

The emerging of MOF materials present opportunities in energy-related fields, such as adsorbents to tackle challenging gas separation processes especially for the industrially important olefin/paraffin separations (Lin et al., Chem, 6(2): 337-63, 2020; Zheng et al., Inorg. Chem., 57:9096, 2018; Li et al., Chem. Soc. Rev., 38(5):1477-1504, 2009; Lin et al., Coord. Chem. Rev., 378:87-103, 2019; Li et al., Science, 362(6413):443-46, 2018; Ma et al., Science, 361(6406): 1008-11, 2018; Lin et al., Coord. Chem. Rev., 384:21-36, 2019; Lin et al., Nat. Mater., 17(12):1128, 2018; Cui et al., Inorganica Chimica Acta, 495:118938, 2019; Lin et al., J. Am. Chem. Soc., 140(40):12940-46, 2018; Li et al., Angew. Chem. Int. Ed., 130(46):15403-08, 2018; Lin et al., J. Am. Chem. Soc., 139(23):8022-28, 2017; Bao et al., Angew. Chem. Int. Ed., 130(49):16252-57, 2018). For example, MOF materials have exhibited attractive separation performance towards the adsorptive separation of ethylene from ethane. Therefore, it is of great significance to fabricate these MOFs in large-scale and economically for practical gas separation.

Mechanochemical synthesis has been recognized as one of the most promising approaches for large-scale production of solid materials, not only because of its high reaction space-time-yield for scale-up but also for their environment-friendly synthetic conditions (e.g., solvent-free) (Rubio-Martinez et al., Chem. Soc. Rev., 46(11):3453-80, 2017; Mottillo et al., Green Chemistry, 19(12):2729-47, 2017; Shi et al., CrystEngComm, 19(30):4265-68, 2017; Friščić et al., Angew. Chem. Int. Ed., 49(4):712-15, 2010; Yuan et al., Angew. Chem. Int. Ed., 49(23):3916-19, 2010; Yuan et al., CrystEngComm, 12(12):4063-65, 2010; Lin et al., Chem. Commun., 47(32):9185-87, 2011; Stojaković et al., Chem. Commun., 48(64):7958-60, 2012). In contrast, conventional synthesis of MOFs are often solvent-intensive with low reaction yield, and involve the production of massive by-products, which limits their industrial applications (Rubio-Martinez et al., Chem. Soc. Rev., 46(11):3453-80, 2017; Mottillo et al., Green Chemistry, 19(12):2729-47, 2017).

Ideally, atom economy is an ultimate approach to achieve high conversion efficiency of the raw chemicals and waste-free during production of MOFs, which is very challenging. Most of mechanochemical synthesis method are achieved by metal salts like metal nitrites or metal chloride, which would result in by-products needed further purification. Alternatively, using metal oxides or metal hydroxides to react with the acidic organic ligands might be a promising approach considering water is the only by-product. However, the high insolubility of metal oxides/hydroxides is very challenging for solid-state reaction. Now only several MOFs have been successfully prepared at room temperature through mechanosynthesis method, but mainly relying on soluble metal salts (Shi et al., CrystEngComm, 19(30):4265-68, 2017; Friščić et al., Angew. Chem. Int. Ed., 49(4):712-15, 2010; Yuan et al., Angew. Chem. Int. Ed., 49(23):3916-19, 2010; Yuan et al., CrystEngComm, 12(12):4063-65, 2010; Lin et al., Chem. Commun., 47(32):9185-87, 2011; Stojaković et al., Chem. Commun., 48(64):7958-60, 2012). Moreover, some metal oxides/hydroxides are relatively inexpensive and of high abundance, which could further reduce the cost and simply the synthetic procedures (Majano et al., Adv. Mater., 25(7):1052-57, 2013; Li et al., Chemistry—A European Journal, 21(18):6913-20, 2015; Crawford et al., Chem. Sci., 6(3):1645-49, 2015; Zhao et al., J. Am. Chem. Soc., 137(43):13756-59, 2015; Maserati et al., Chem. Mater., 28(5):1581-88, 2016; Julien et al., J. Am. Chem. Soc., 138(9):2929-32, 2016.

Previous studies on the ultramicroporous metal-organic framework [$Ca(C_4O_4)(H_2O)$] (UTSA-280) have shown this MOF to be selective for ethylene separation (Lin et al., Nat. Mater., 17(12):1128, 2018 and WO 2019/183635, both of which are incorporated by reference herein in their entireties).

Ethylene/ethane separation is an important process in the petrochemical industry, giving a worldwide ethylene production exceeding 150 million metric tons in 2016. Due to the very similar sizes and volatilities of these hydrocarbon molecules, the purification of ethylene is currently accomplished by repeated distillation-compression cycling of the mixture under harsh conditions in huge splitter column of over 100 trays. Such well-established industrial separation technology is one of the most energy-intensive processes in the chemical industry, which highly relies on thermal energy and consumes ten times energy than membrane-based separation technologies or other non-thermal ones (Sholl et al., 2016 and Chu et al., 2017). For substituting the cryogenic distillation processes, exploration of new adsorptive separation technologies based on porous materials is dramatically driven by the potential of tremendous energy savings. As customizable porous materials, metal-organic frameworks (MOFs) are highly versatile in pore engineering, affording precise tuning and functionalization of the pore structure (Kitagawa, 2015 and Furukawa et al., 2013), and thus have been intensively investigated as excellent adsorbents for selective gas separation (Bloch et al., 2012, Yang et al., 2014, Cadiau et al., 2016, Cui et al., 2016, Liao et al., 2017, Yoon et al., 2016, and Vaidhyanathan et al., 2010). But for ethylene/ethane separation, there is a major barrier in improving the selectivity for separating these gases because of their very similar physical properties. Various functionalized MOF adsorbents, including those feature open metal sites that help enhancing the olefin binding affinity, have been explored to overcome this challenge (He et al., 2012 and Zhai et al., 2016). However, their unavoidable co-adsorption of analogous alkanes is unfavorable for efficient olefin purification via swing adsorption or membrane-based methods, let alone other problems associated with their active metal sites, which involves the recovery of adsorbent and olefin products (high energy consumption and possible olefin polymerization) (Ji et al., 2017 and Klet et al., 2015), and water/humidity stability issues.

Ideal separation approaches like molecular sieving, allows complete separating one component from others based on molecular size or shape cut-off, which avoids the co-adsorption of impurity without sacrificing the valuable uptake capacity of porous media and gives infinite selectivity that is beneficial to membrane-based separation (Lin, 2016 and Peng et al., 2014). Similar separation process such as potassium ions transport existing in cell-membranes of biological systems involves excluding sodium ions despite their size difference in ionic radius of sub-angstrom level (0.038 nm), giving extremely precise selectivity that can also be observed in crown ether/cryptand-ion systems. Accordingly, precise size/shape-matching is vital toward specific recognition of olefin/paraffin (Pan et al., 2006 and Ma et al., 2009). Considering the even smaller shape difference between olefin and paraffin (only 0.028 nm in kinetic diameters for ethylene/ethane) and their identical physical properties (FIG. 1 and Table 1), it is particularly challenging to design MOFs as molecular sieves for this gas separation. Extensive research endeavors have been pursued to make tailor-made MOFs for specific molecular sieving of some important hydrocarbons (Cadiau et al., 2016, Cui et al., 2016, and Bao et al., 2016), but it is yet to be shown that MOFs can sieve ethylene while completely exclude ethane.

TABLE 1

Comparison of physical parameters of $C_2H_4$ and $C_2H_6$ (Li et al., 2009).

| Compound | Molecular Weight (g/mol) | Kinetic Diameter (Å) | Boiling points (K) | Polarizability ($10^{-25}$ cm$^3$) | Dipole moment ($10^{-18}$ esu cm) | Quadruple moment ($10^{-26}$ esu cm$^2$) |
|---|---|---|---|---|---|---|
| $C_2H_4$ | 28.05 | 4.163 | 169.4 | 42.5 | 0 | 1.5 |
| $C_2H_6$ | 30.07 | 4.443 | 184.5 | 44.3-44.7 | 0 | 0.65 |

Given the usefulness of materials that can effectively separate industrial feedstocks, such as ethylene from ethane, in order to obtain purer ethylene and/or purer ethane, materials that can achieve these separations are of great importance, including methods and processes to fabricate these MOFs, for example, in a large-scale, environmentally friendly, and/or economically manner.

SUMMARY

In some aspects, the present disclosure provides methods of preparing a metal organic framework (MOF) comprising a repeat unit of the formula:

[Ca(C$_4$O$_4$)(H$_2$O)]      (I)

or a hydrate thereof, comprising:

a) obtaining a first reagent, wherein the first reagent is CaO, Ca(OH)$_2$, or a combination thereof; and b) admixing the first reagent with squaric acid under conditions suitable to form the MOF of formula I.

In some embodiments, the admixing comprising a mechanochemical process. In some embodiments, the mechanochemical process comprises grinding the admixture of the first reagent and the squaric acid. In some embodiments, the conditions comprise the presence of water. In some embodiments, the molar ratio of the water to the first reagent is from about 1:1 to about 10:1. In some of these embodiments, the molar ratio is about 5:1.

In some embodiments, the admixing step is conducted in the absence of any organic solvents. In some embodiments, the method does not generate any stoichiometric quantities of salt byproducts. In some embodiments, the admixing is conducted at a temperature from about 0° C. to about 30° C.

In some embodiments, the first reagent is CaO. In some of these embodiments, the molar ratio of CaO to squaric acid is about 1:1. In other embodiments, the first reagent is Ca(OH)$_2$.

In some embodiments, the $C_4O_4^{2-}$ group is of the formula:

(A)

In some embodiments, the methods further comprise washing the MOF after the admixing step. In some of these embodiments, the MOF is washed with methanol.

In some embodiments, the methods further comprise activating the MOF. In some of these embodiments, the MOF is activated by heating the MOF at a temperature from about 50° C. to about 300° C. In some of these embodiments, the temperature is about 100° C. In some of these embodiments, the heating of the MOF is conducted under vacuum.

In some embodiments, the methods provided herein may be used to prepare more than one kilogram of the MOF. In some of these embodiments, the methods may be used to prepare more than ten kilograms of the MOF. In some of these embodiments, the methods may be used to prepare more than one hundred kilograms of the MOF. In some of these embodiments, the methods may be used to prepare more than one thousand kilograms of the MOF. In some of these embodiments, the methods may be used to prepare more than ten thousand kilograms of the MOF. In some embodiments, the method may be used to prepare from about one kilogram to about one hundred kilograms of the MOF.

In another aspect, the present disclosure provides metal organic frameworks (MOFs) prepared by any of the methods outlined above or exemplified below.

In another aspect, the present disclosure provides MOFs which may be used to remove one type of molecules from a mixture. In one aspect, the present disclosure provides methods of separating two or more compounds using a metal organic framework prepared by mechanochemical synthesis, wherein the MOF comprises a repeating unit of the formula ML, wherein M is a divalent metal ion and L is a ligand of the formula:

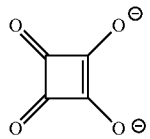

(I)

or a hydrate thereof, wherein the method comprises:
(A) combining the metal-organic framework with a mixture comprising a first compound and a second compound; and
(B) separating the first compound from the second compound within the metal-organic framework.

In some embodiments, M is a divalent alkali earth metal such as Ca(II). In some embodiments, the metal organic framework is further defined as a metal organic framework of the formula: $M(H_2O)L$ such as by the formula: $Ca(H_2O)L$.

In some embodiments, the first compound or the second compound is a gas molecule. Alternatively, in some embodiments, both the first and second compounds are gas molecules. In some embodiments, the first compound is an alkene$_{(C \leq 8)}$ such as ethylene. In other embodiments, the first compound is an alkyne$_{(C \leq 8)}$ such as ethyne. In still other embodiments, the first compound is $CO_2$. In some embodiments, the second compound is an alkane$_{(C \leq 8)}$ such as ethane or methane. In other embodiments, the second compound is $N_2$.

In some embodiments, the mixture comprises from about 1:999 to about 1:1 of the first compound to the second compound. In other embodiments, the mixture comprises from about 1:999 to about 1:1 of the second compound to the first compound. In some embodiments, the mixture comprises about 1:99 of the first compound to the second compound. In some embodiments, the separation is carried out at a pressure from about 0.1 bar to about 10 bar such as at a pressure of about 1 bar.

In some embodiments, the metal-organic framework is adhered to a fixed bed surface. In some embodiments, the separation is carried out in an absorber packed with the metal-organic framework. In some embodiments, the separation is carried out at a temperature from about 0° C. to about 75° C. such as at about room temperature.

In still another aspect, the present disclosure provides a method of separating ethylene from a mixture of ethane and ethylene comprising exposing the mixture to a metal organic framework as described herein.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

$$S_{BET} = \frac{v_m Ns}{Va} = \frac{Ns}{(A+I)Va} = 6.023 \times 10^{23} \times 0.195 \times$$
$$10^{-18} / ((0.01681 - 0.00037269) \times 0.0797 \times 22414) = 319.2 \, m^2/g;$$

Figure 6:
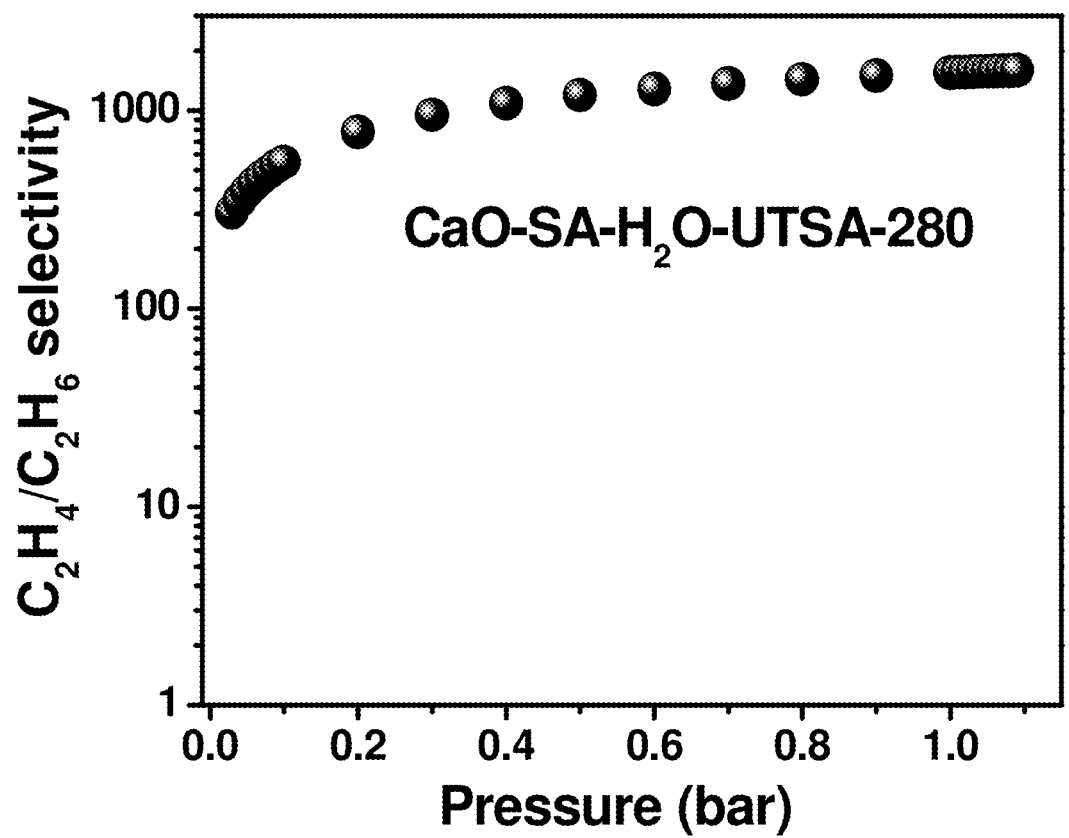

FIG. 6. IAST adsorption selectivity of as-synthesized UTSA-280 for an equimolar ethylene/ethane mixture at 298 K.

Figure 7:
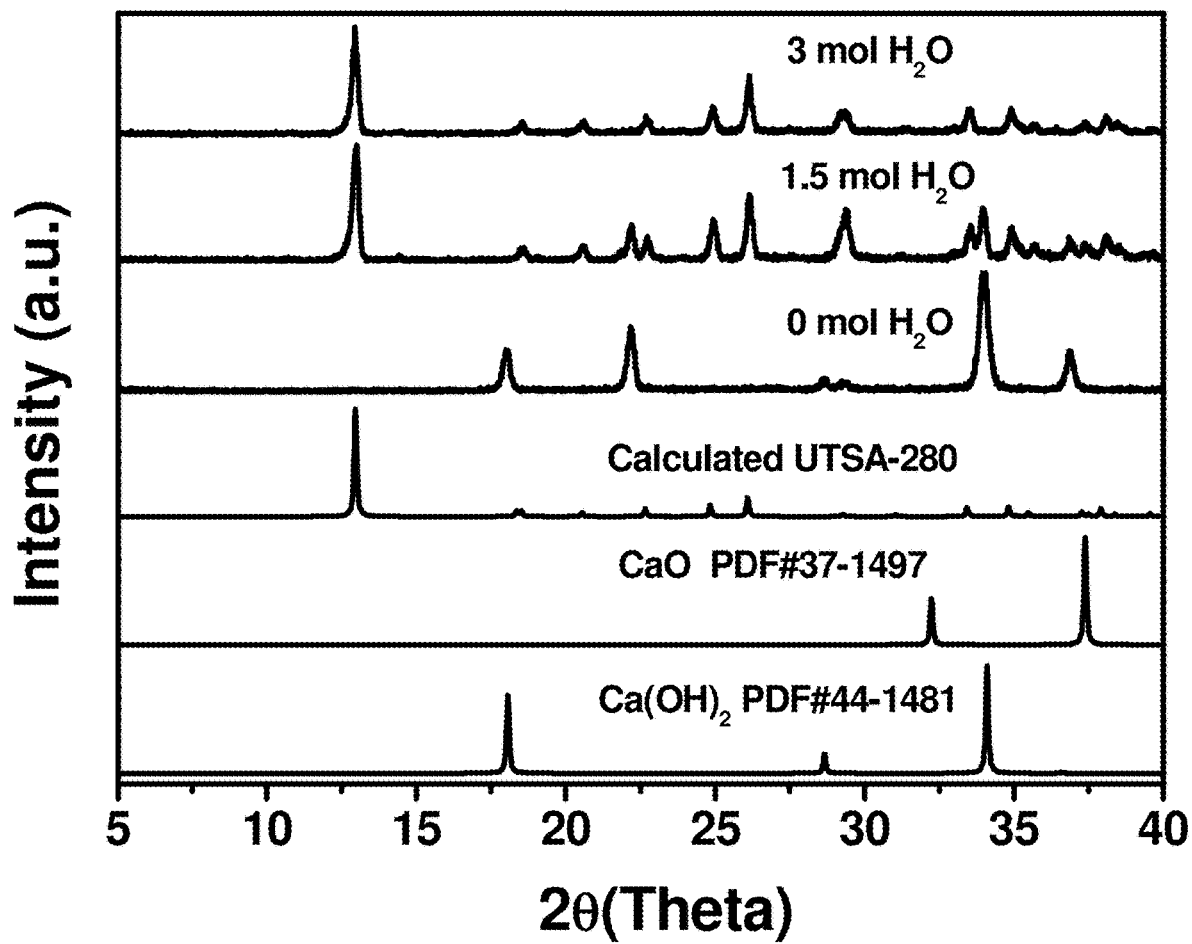

FIG. 7. UTSA-280 prepared with varied amounts of water in stoichiometric mixture of $Ca(OH)_2$ and SA.

Figure 8:
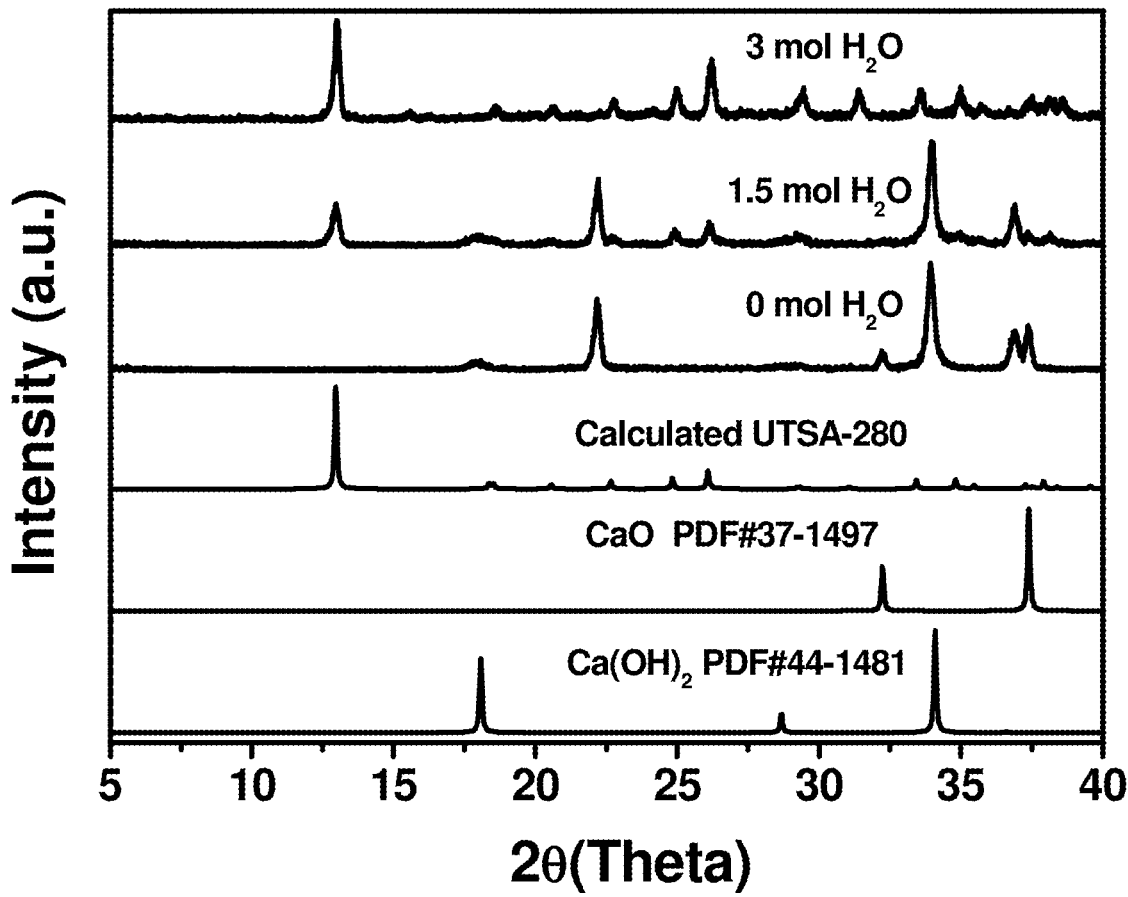

FIG. 8. UTSA-280 prepared at varied amounts of water in stoichiometric mixture of CaO and SA.

Figure 9:
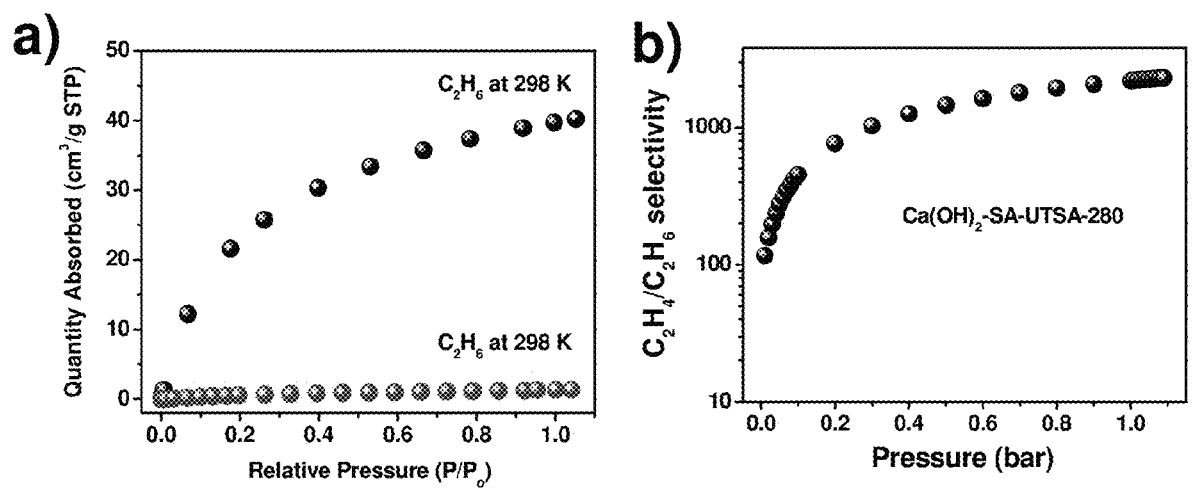

FIG. 9. a) Single-component sorption isotherms of ethylene (black), ethane (red) at 98 K for as-synthesized UTSA-280 synthesized from $Ca(OH)_2$ and squaric acid; b) IAST adsorption selectivity for an equimolar ethylene/ethane mixture at 298 K.

Figure 10:
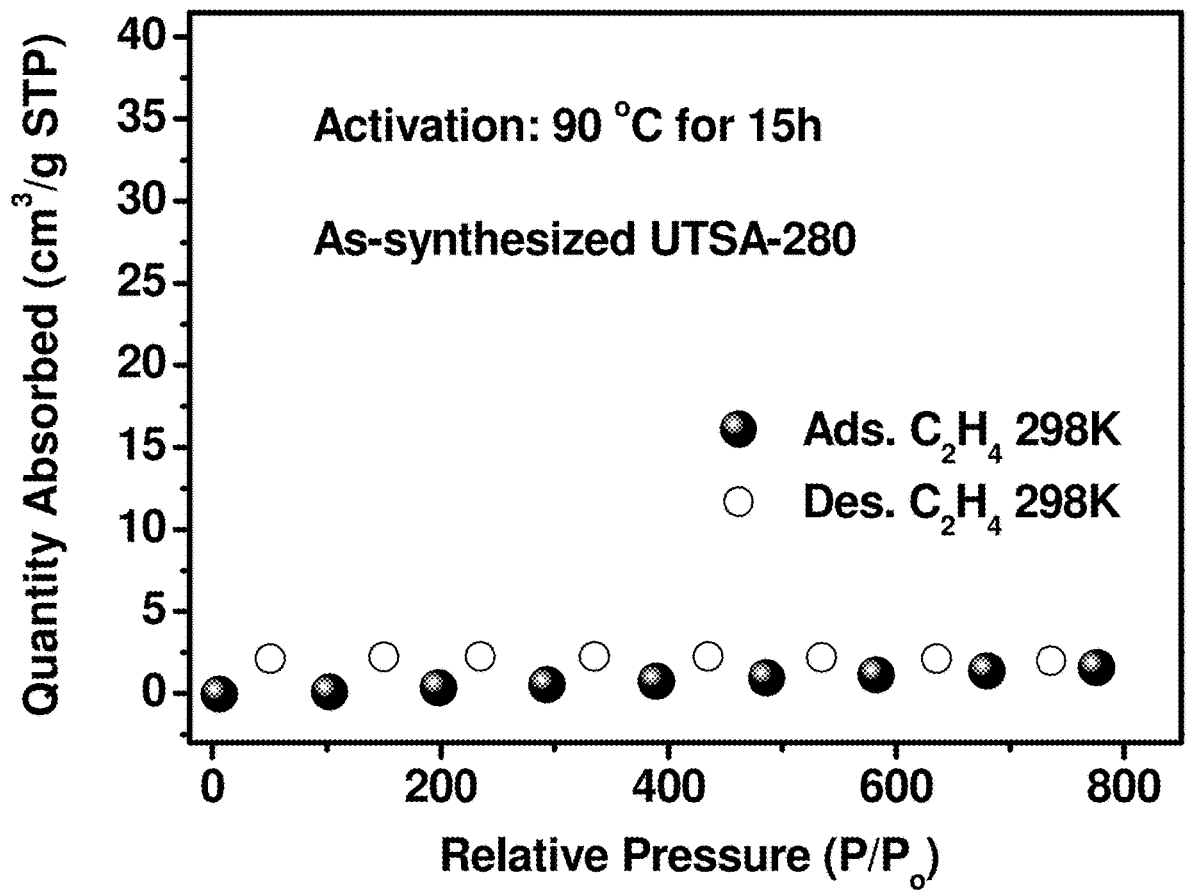

FIG. 10. Single-component sorption isotherms of ethylene at activation conditions of 90° C. for 15 h.

Figure 11:
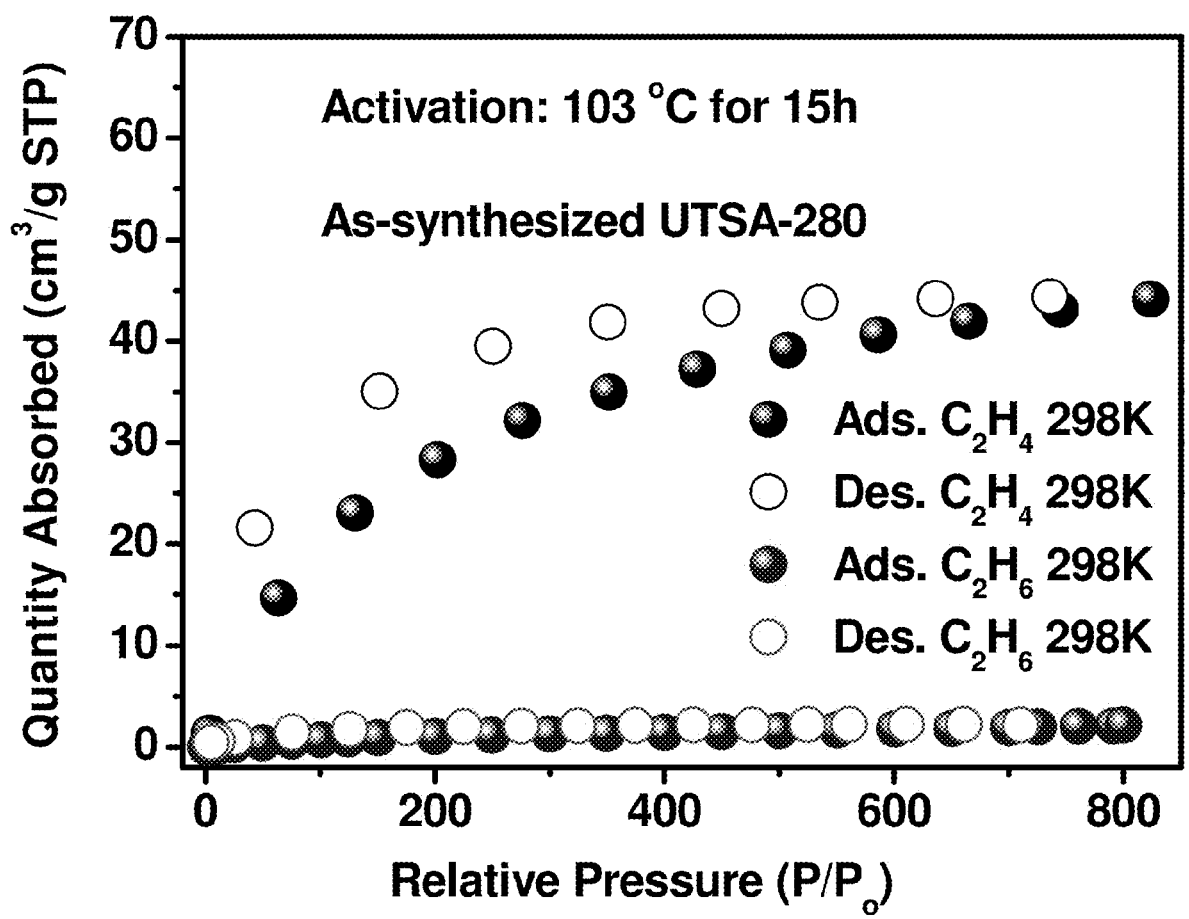

FIG. 11. Single-component sorption isotherms of ethylene and ethane at activation conditions of 103° C. for 12 h.

Figure 12:
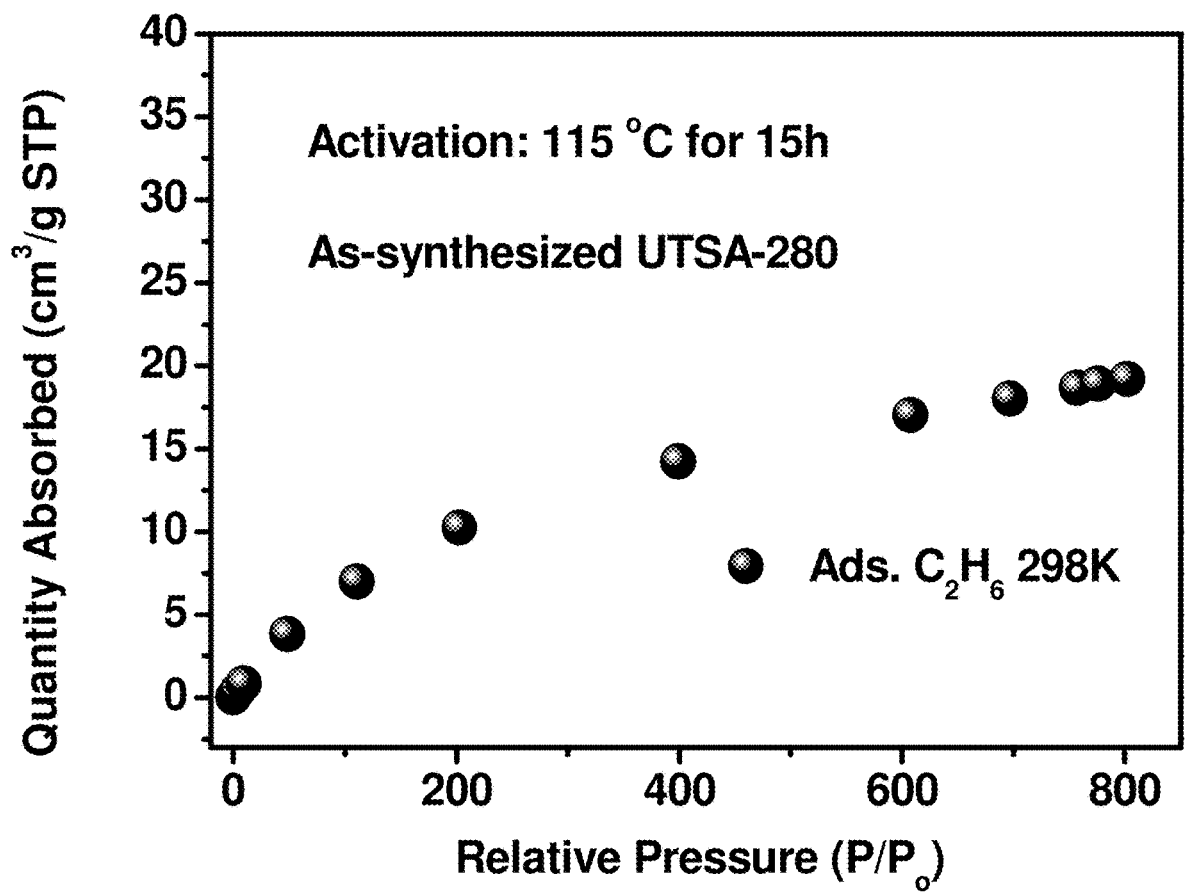

FIG. 12. Single-component sorption isotherms of overactivated sample for ethylene and ethane at 115° C. for 15 h.

Figure 13:
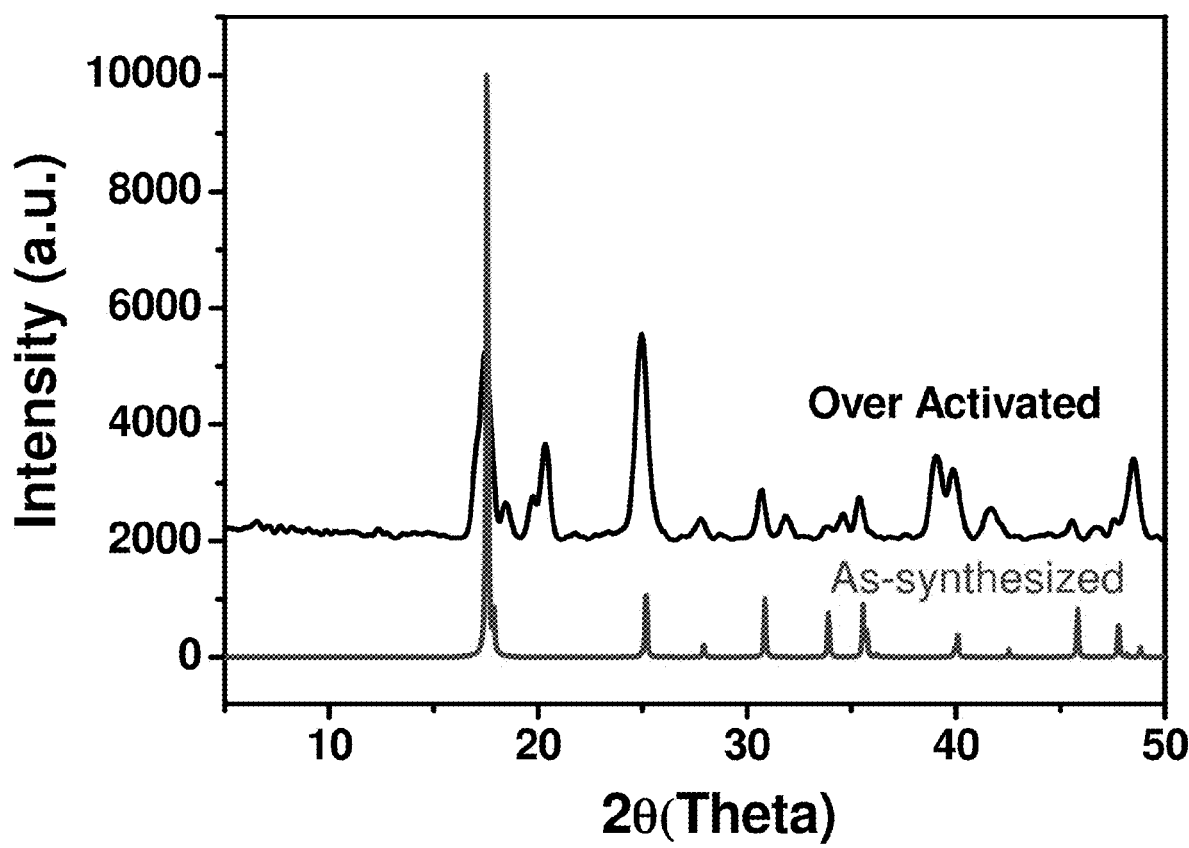

FIG. 13. Powder neutron diffraction data for over activated UTSA-280 sample under dynamic vacuum of $<10^{-7}$ bar.

DESCRIPTION OF ILLUSTRATIVE EMBODIMENTS

Provided herein are methods for preparing metal-organic frameworks (MOFs) of the formula: ML wherein L is squaric acid and which exhibits pore sizes sufficient to host guest gas molecules and/or to separate a first compound from a mixture of compounds. In some embodiments, these metal-organic frameworks, e.g., UTSA-280, may be used to separate one gas molecule from a mixture of two or more gas molecules such as ethylene and ethane. In some embodiments, the UTSA-280 may be prepared via mechanochemical synthesis, including at a large scale and/or under environmentally friendly conditions.

Provided herein are methods for separating a first compound from a mixture of compounds using metal-organic frameworks of the formula: ML wherein L is squaric acid and which exhibits pore sizes sufficient to host guest gas molecules. In some embodiments, these metal-organic frameworks may be used to separate one gas molecule from a mixture of two or more gas molecules such as ethylene and ethane. In some embodiments, the metal-organic framework is [Ca(C$_4$O$_4$)(H$_2$O)] (termed as UTSA-280) that feature one dimensional specific ethylene channels, exhibiting exclusion of ethane from ethylene under ambient condition. In some embodiments, the material used herein exhibit channel spaces that enable recognition of ethylene molecules of high packing intensity and selectivity with ethylene productivity of 1.7 mol/kg at ambient condition. Additionally, the material may in some embodiments be easily regenerated under mild conditions because of its low adsorption heat.

I. METHODS OF PREPARING MOFS

In some aspects, the present disclosure provides methods of preparing a metal organic framework (MOF) comprising a repeat unit of the formula:

[Ca(C$_4$O$_4$)(H$_2$O)]      (I)

or a hydrate thereof, comprising:
 a) obtaining a first reagent, wherein the first reagent is CaO, Ca(OH)$_2$, or a combination thereof; and
 b) admixing the first reagent with squaric acid under conditions suitable to form the MOF of formula I.

In some embodiments, the admixing comprising a mechanochemical process. In some embodiments, the mechanochemical process comprises grinding the admixture of the first reagent and the squaric acid. In some embodiments, the squaric acid is raw. In some embodiments, the conditions comprise the presence of water. In some embodiments, the molar ratio of the water to the first reagent is from about 1:1 to about 10:1. In some of these embodiments, the molar ratio is about 5:1.

In some embodiments, the admixing step is conducted in the absence of any organic solvents. In some embodiments, the method does not generate any stoichiometric quantities of salt byproducts. In some embodiments, the admixing is conducted at a temperature from about 0° C. to about 30° C.

In some embodiments, the first reagent is CaO. In some of these embodiments, the molar ratio of CaO to squaric acid is about 1:1. In other embodiments, the first reagent is Ca(OH)$_2$.

In some embodiments, the C$_4$O$_4{}^{2-}$ group is of the formula:

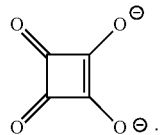

(A)

In some embodiments, the methods further comprise washing the MOF after the admixing step. In some of these embodiments, the MOF is washed with methanol.

In some embodiments, the methods further comprise activating the MOF. In some of these embodiments, the MOF is activated by heating the MOF at a temperature from about 50° C. to about 300° C. In some of these embodiments, the temperature is about 100° C. In some of these embodiments, the heating of the MOF is conducted under vacuum.

In another aspect, the present disclosure provides metal organic frameworks (MOFs) prepared by any of the methods outlined above or exemplified below. In some embodiments, UTSA-280 is successfully prepared by using calcium oxide (CaO) or calcium hydroxide (Ca(OH)$_2$) through mechanochemical synthesis method, which, for example, offers a facile, controlled, economic and/or environment-friendly approach for large scale production. The UTSA-280 thereby has been verified by powder X-ray diffraction patterns (PXRD), scanning electron microscope (SEM) and gas sorption experiments. In some embodiments, the present disclosure provides a facile and environment-friendly synthetic method of UTSA-280 through mechanochemical synthesis using Ca(OH)$_2$ and/or CaO to react with squaric acid. In some embodiments, the resultant UTSA-280 shows good separation performance for ethylene/ethane. In some embodiments, the disclosure provides an approach for the scaled-up synthesis of UTSA-280.

The methods of the present invention are shown, for example, above, in the summary of the invention section, and in the claims below. The MOF's discussed herein may be made using the synthetic methods outlined in the Examples section. These methods can be further modified and optimized using the principles and techniques of chemistry as applied by a person skilled in the art. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

II. METHODS OF CHEMICAL SEPARATION USING MOFS

In another aspect, the present disclosure provides MOFs which may be used to remove one type of molecules from a mixture. In one aspect, the present disclosure provides methods of separating two or more compounds using a metal organic framework prepared by mechanochemical synthesis, wherein the MOF comprises a repeating unit of the formula ML, wherein M is a divalent metal ion and L is a ligand of the formula:

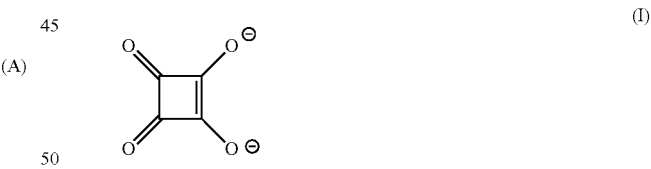

(I)

or a hydrate thereof, wherein the method comprises:
 (A) combining the metal-organic framework with a mixture comprising a first compound and a second compound; and
 (B) separating the first compound from the second compound within the metal-organic framework.

In some embodiments, M is a divalent alkali earth metal such as Ca(II). In some embodiments, the metal organic framework is further defined as a metal organic framework of the formula: M(H$_2$O)L such as by the formula: Ca(H$_2$O)L.

In some embodiments, the first compound or the second compound is a gas molecule. In some of these embodiments, both the first and second compounds are gas molecules. In some embodiments, the first compound is an alkene$_{(C\leq 8)}$ such as ethylene. In other embodiments, the first compound is an alkyne$_{(C \leq 8)}$ such as ethyne. In some of these embodiments, the $C_2H_4/C_2H_6$ selectivity of UTSA-280 is infinite. Therefore, the methods of the present disclosure may facilitate almost complete removal of ethane from ethylene. In still other embodiments, the first compound is $CO_2$. In some embodiments, the second compound is an alkane$_{(C \leq 8)}$ such as ethane or methane. In other embodiments, the second compound is $N_2$.

In some embodiments, the mixture comprises from about 1:999 to about 1:1 of the first compound to the second compound. In other embodiments, the mixture comprises from about 1:999 to about 1:1 of the second compound to the first compound. In some embodiments, the mixture comprises about 1:99 of the first compound to the second compound. In some embodiments, the separation is carried out at a pressure from about 0.1 bar to about 10 bar such as at a pressure of about 1 bar.

In some embodiments, the metal-organic framework is adhered to a fixed bed surface. In some embodiments, the separation is carried out in an absorber packed with the metal-organic framework. In some embodiments, the separation is carried out at a temperature from about 0° C. to about 75° C. such as at about room temperature.

In still another aspect, the present disclosure provides a method of separating ethylene from a mixture of ethane and ethylene comprising exposing the mixture to a metal organic framework as described herein.

III. DEFINITIONS

"Metal-organic frameworks" (MOFs) are framework materials, typically three-dimensional, self-assembled by the coordination of metal ions with organic linkers exhibiting porosity, typically established by gas adsorption. The MOFs discussed and disclosed herein are at times simply identified by their repeat unit as defined below without brackets or the subscript n. A mixed-metal-organic frameworks (M'MOF) is a subset of MOFs having two of more types of metal ions.

The term "unit cell" is basic and least volume consuming repeating structure of a solid. The unit cell is described by its angles between the edges ($\alpha$, $\beta$, $\gamma$) and the length of these edges (a, b, c). As a result, the unit cell is the simplest way to describe a single crystal X-ray diffraction pattern.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerization, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc. Note that for MOFs the repeat unit may also be shown without the subscript n.

"Pores" or "micropores" in the context of metal-organic frameworks are defined as open space within the MOFs; pores become available, when the MOF is activated for the storage of gas molecules. Activation can be achieved by heating, e.g., to remove solvent molecules.

"Multimodal size distribution" is defined as pore size distribution in three dimensions.

"Multidentate organic linker" is defined as ligand having several binding sites for the coordination to one or more metal ions.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Additionally, it is contemplated that one or more of the metal atoms may be replaced by another isotope of that metal. In some embodiments, the calcium atoms can be $^{40}Ca$, $^{42}Ca$, $^{43}Ca$, $^{44}Ca$, $^{46}Ca$, or $^{48}Ca$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on a carbon atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

The term "saturated" when referring to an atom means that the atom is connected to other atoms only by means of single bonds.

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2H$); "halo" means independently —F, —Cl, —Br or —I; "amino" means —$NH_2$; "hydroxyamino" means —NHOH; "nitro" means —$NO_2$; imino means =NH; "cyano" means —CN; "isocyanyl" means —N=C=O; "azido" means —$N_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "thiocarbonyl" means —C(=S)—; "sulfonyl" means —S(O)$_2$—; and "sulfinyl" means —S(O)—.

In the context of chemical formulas, the symbol "—" means a single bond, "=" means a double bond, and "≡"

means triple bond. The symbol "- - -" represents an optional bond, which if present is either single or double. The symbol "====" represents a single bond or a double bond. Thus, the formula

covers, for example,

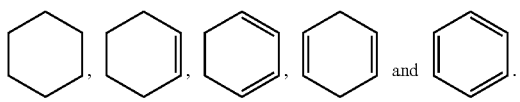

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "▫▫▫▫" means a single bond where the group attached to the thick end of the wedge is "into the page". The symbol "∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M-C, M=C, M- - -C, and M====C, each refers to a bond of any and type and order between a metal atom and a carbon atom.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "alkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C$_{1-4}$-alkyl", "C1-4-alkyl", "alkyl$_{(C1-4)}$", and "alkyl$_{(C≤4)}$" are all synonymous. Except as noted below, every carbon atom is counted to determine whether the group or compound falls with the specified number of carbon atoms. For example, the group dihexylamino is an example of a dialkylamino$_{(C12)}$ group; however, it is not an example of a dialkylamino$_{(C6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$ Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

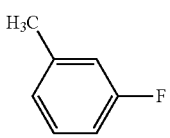

is also taken to refer to

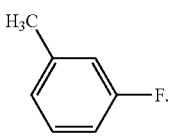

Aromatic compounds may also be depicted using a circle to represent the delocalized nature of the electrons in the fully conjugated cyclic π system, two non-limiting examples of which are shown below:

The term "alkyl" refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

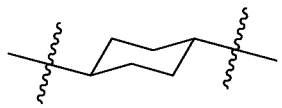

is a non-limiting example of cycloalkanediyl group. A "cycloalkane" refers to the class of compounds having the formula H—R, wherein R is cycloalkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, CH$_2$CH=CH$_2$ (allyl), —CH$_2$CH=CHCH$_3$, and —CH=CHCH=CH$_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

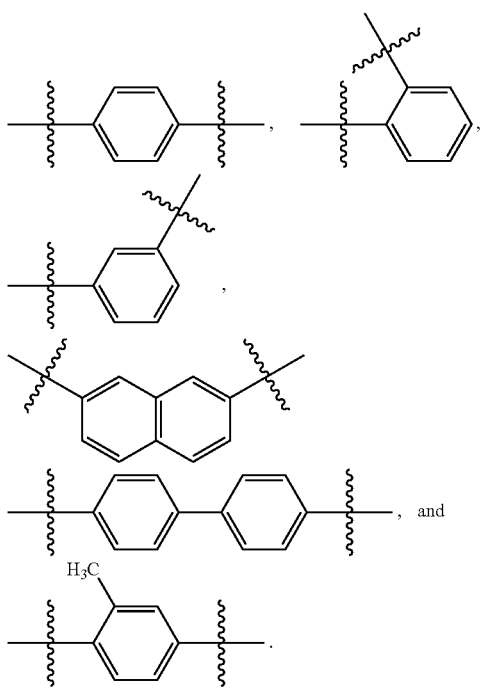

An "arene" refers to the class of compounds having the formula H—R, wherein R is aryl as that term is defined above. Benzene and toluene are non-limiting examples of arenes.

The term "acyl" refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "alkoxy" refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

When a chemical group is used with the "substituted" modifier, one or more hydrogen atom has been replaced, independently at each instance, by —OH, —F, —Cl, —Br, —I, —NH$_2$, —NO$_2$, —CO$_2$H, —CO$_2$CH$_3$, —CO$_2$CH$_2$CH$_3$, —CN, —SH, —OCH$_3$, —OCH$_2$CH$_3$, —C(O)CH$_3$, —NHCH$_3$, NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. For example, the following groups are non-limiting examples of substituted alkyl groups: —CH$_2$OH, —CH$_2$C$_1$, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, CH$_2$N(CH$_3$)$_2$, and —CH$_2$CH$_2$C$_1$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$C$_1$ is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups. Non-limiting examples of substituted aralkyls are: (3-chlorophenyl)-methyl, and 2-chloro-2-phenyl-eth-1-yl. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups. The groups —NHC(O)OCH$_3$ and —NHC(O)NHCH$_3$ are non-limiting examples of substituted amido groups.

The above definitions supersede any conflicting definition in any of the reference that is incorporated herein by reference. The fact that certain terms are defined, however, should not be considered as indicative that any term that is undefined is indefinite. Rather, all terms used are believed to describe the invention in terms such that one of ordinary skill can appreciate the scope and practice the present invention.

III. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Mechanochemical Synthesis of Ethylene Sieve UTSA-280

Chemicals: Calcium oxide (CaO, Lab Grade, Fisher Chemical), Calcium nitrate tetrahydrate (Ca(NO$_3$)$_2$.4H$_2$O, 99%, Fisher Chemical), sodium hydroxide (NaOH, 98%, Alfa Aesar), squaric acid (or 3,4-dihydroxycyclobut-3-ene-1,2-dione, (Oakwood Chemicals), were purchased and used without further purification. CO$_2$ (99.999%), C$_2$H$_4$ (99.5%), C$_2$H$_6$ (99.5%), He (99.999%) were purchased form Airgas.

Synthesis of [Ca(C$_4$O$_4$)(H$_2$O)].xH$_2$O: The synthesis of UTSA-280 was performed from 1:1 ratio of solid mixture of CaO (20.0 mmol, 1.122 g) and squaric acid (20 mmol, 2.281 g) and H$_2$O (100 mmol, 1.6 mL) under grinding in a mortar for around 1 minute.

Synthesis of kilogram-scale [Ca(C$_4$O$_4$)(H$_2$O)].xH$_2$O: The kilogram-scale synthesis of UTSA-280 was performed from 1:1 ratio of solid and well-mixed powders of CaO (1.43 mol, 80.08 g) and squaric acid (1.43 mol, 163.1 g) in a 1000 mL beaker. Then ultrapure DI H$_2$O (10.0 mol, 180 mL) was added under continuous stirring and the reaction was under stirring for around 10 minutes. The obtained sample can be air-dry under room temperature in some embodiments. This reaction can proceed in large scale with the presence of water and continued stirring or grinding in some embodiments. And both the conversion and percent yield are around 100%.

Single component gas sorption measurement: The gas sorption isotherms were collected on an automatic volumetric adsorption apparatus (Micromeritics ASAP 2020 surface area analyzer). Prior to the sorption measurements, the as-synthesized sample was washed with methanol for three times and placed in a quartz tube and dried under high vacuum for 15 hours at 103° C. (at rate of 2° C./min, under $1\times10^{-5}$ bar, i.e. 8 µm Hg) to remove the guest water molecules, giving the activated UTSA-280 for gas sorption analyses.

The activation temperatures and times can vary from the previous reported condition regarding the different size of particles. Also, insufficient activation might happen at relatively low heating temperatures or for not enough time that all leading to little amount of gas uptakes, whereas over activation would happen at relatively high temperatures, under higher vacuum, or for excess heating time that can cause partial loss of the coordinated water, further decreasing the molecular sieving effects. See Lin et al., *Nat. Mater.*, 17(12):1128, 2018 and WO 2019/183635, both of which are incorporated by reference herein in their entireties.

SEM and X-ray diffraction analysis of powder samples: Scanning Electron microscopy (SEM) images were obtained using Hitachi 55500 device at an accelerating voltage of 20 kV. Powder X-ray diffraction patterns were collected using a Rigaku Ultima IV diffractometer (Cu Kα λ=1.540598 Å) with an operating power of 40 kV, 44 mA and a scan rate of 10.0°/min. The data were collected in the range of 2θ=5-40°. In-situ powder X-ray diffraction patterns were collected using a Bruker D8 ADVANCE X-ray diffractometer equipped with an XRK high-temperature chamber and the high vacuum line under an operating power of 40 kV, 40 mA for Cu Kα radiation.

IAST calculations of adsorption selectivities: The adsorption selectivity for $C_2H_4/C_2H_6$ separation is defined by the equation:

$$S_{ads} = \frac{q_1/q_2}{p_1/p_2}$$

$q_1$, and $q_2$ are the molar loadings in the adsorbed phase in equilibrium with the bulk gas phase with partial pressures $p_1$, and $p_2$.

Results: UTSA-280 is an ultramicroporous metal-organic framework constructed from calcium(II) and squarate ($C_4O_4^{2-}$) through coordinative linkages, showing three-dimensional frameworks with rigid one-dimensional open channels that exhibits high sieving separation of ethylene from ethane. The previous synthetic method of [$Ca(C_4O_4)$($H_2O$)] was demonstrated by reaction between soluble calcium nitrate tetrahydrate ($Ca(NO_3)_2 \cdot 4H_2O$) and sodium squarate ($Na_2C_4O_4$) through either solution diffusion or direct mixing, which not only consumes large amount of water but also produces lots of by-products such as $NaNO_3$. See Lin et al., *Nat. Mater.*, 17(12):1128, 2018 and WO 2019/183635, both of which are incorporated by reference herein in their entireties.

Figure 1:
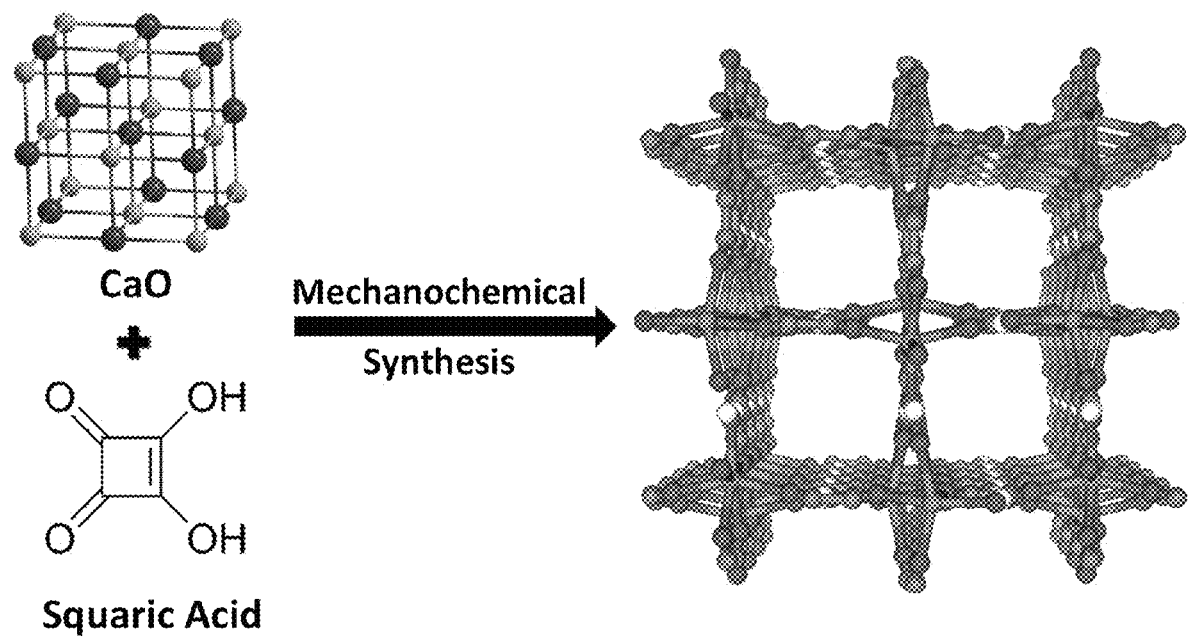
FIG. 1. Mechanochemical synthesis for preparation of UTSA-280.

In order to replace the $Ca(NO_3)_2 \cdot 4H_2O$, as shown in FIG. 1, the current synthetic method targets on the accessible and abundant CaO or $Ca(OH)_2$, which are more easily obtained from industrial calcination of $CaCO_3$ that is of great abundance on earth. Therefore, the use of soluble calcium salts prepared from reactions of metal oxides with corrosive and toxic acids (HCl or $HNO_3$) can be avoided. And there is no need of using NaOH as strong base for deprotonation of squaric acid to obtain precursor solution of sodium squarate ($Na_2C_4O_4$). Considering squaric acid is a relatively strong acid with $pK_{a1}=1.5$ and $pK_{a2}=3.4$ while $Ca(OH)_2$ is a strong base, direct acid-base reaction between $Ca(OH)_2$ and squaric acid in solid state might be applicable for UTSA-280 in terms of the chemical compositions. In this context, water is the only by-product. Thus, mechanochemical synthesis of stoichiometric ratio of $Ca(OH)_2$ with squaric acid has been performed at room temperature.

Figure 2:
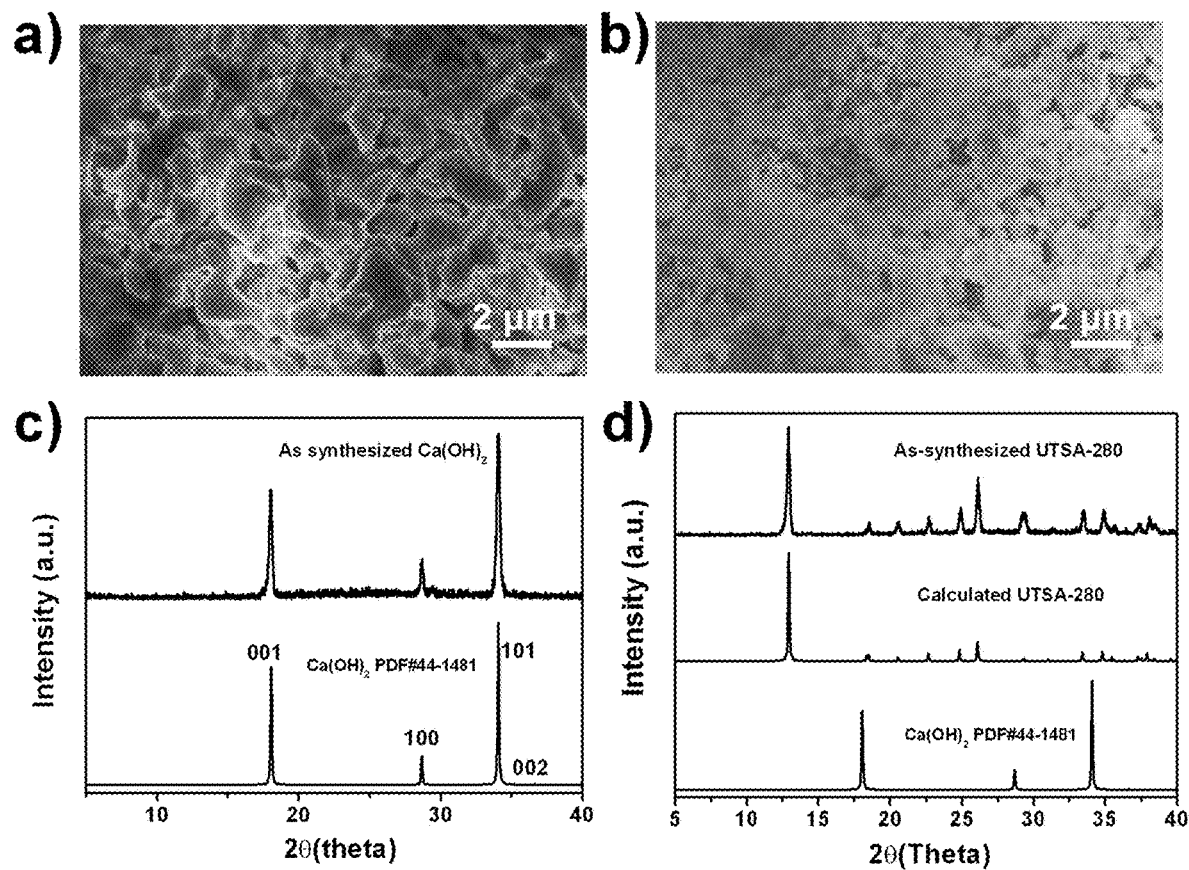
FIG. 2. SEM images and PXRD patterns of raw $Ca(OH)_2$ (a,c) and as-synthesized UTSA-280 (b,d).

Interestingly, the reaction did happen under grinding of the two mixtures with presence of little amount of water in a mortar. The reaction has been performed completely within only a few minutes (FIG. 2). As shown in SEM images (FIG. 2), $Ca(OH)_2$ particles with random morphologies were utilized to react with squaric acid to produce as-synthesized UTSA-280 particles exhibiting uniform morphology with particle sizes of around 0.5-3 µm, which is smaller than those from the previous solution method. See Mottillo et al., *Green Chemistry*, 19(12):2729-47, 2017, which is incorporated herein by reference in its entirety. PXRD pattern of as-synthesized UTSA-280 indicate the high crystallinity and purity of UTSA-280. It should be noted that the presence of water is essential for promoting the reaction in some embodiments. Therefore, systematic experiments have been conducted to optimize the amount of water for complete reaction of $Ca(OH)_2$ and squaric acid. As shown in FIG. 7, there is no formation of UTSA-280 without addition of water. Adding 1.5 mol/mol water to mixture of $Ca(OH)_2$ and squaric acid, the peaks of UTSA-280 gradually appeared and the peaks of $Ca(OH)_2$ would then be weakened and finally disappeared from the PXRD pattern, which indicated the conversion from $Ca(OH)_2$ and squaric acid to the as-synthesized UTSA-280. Further increasing of the water molar ratio to 3, $Ca(OH)_2$ disappeared completely, while UTSA-280 with high crystallinity gradually appeared.

Figure 3:
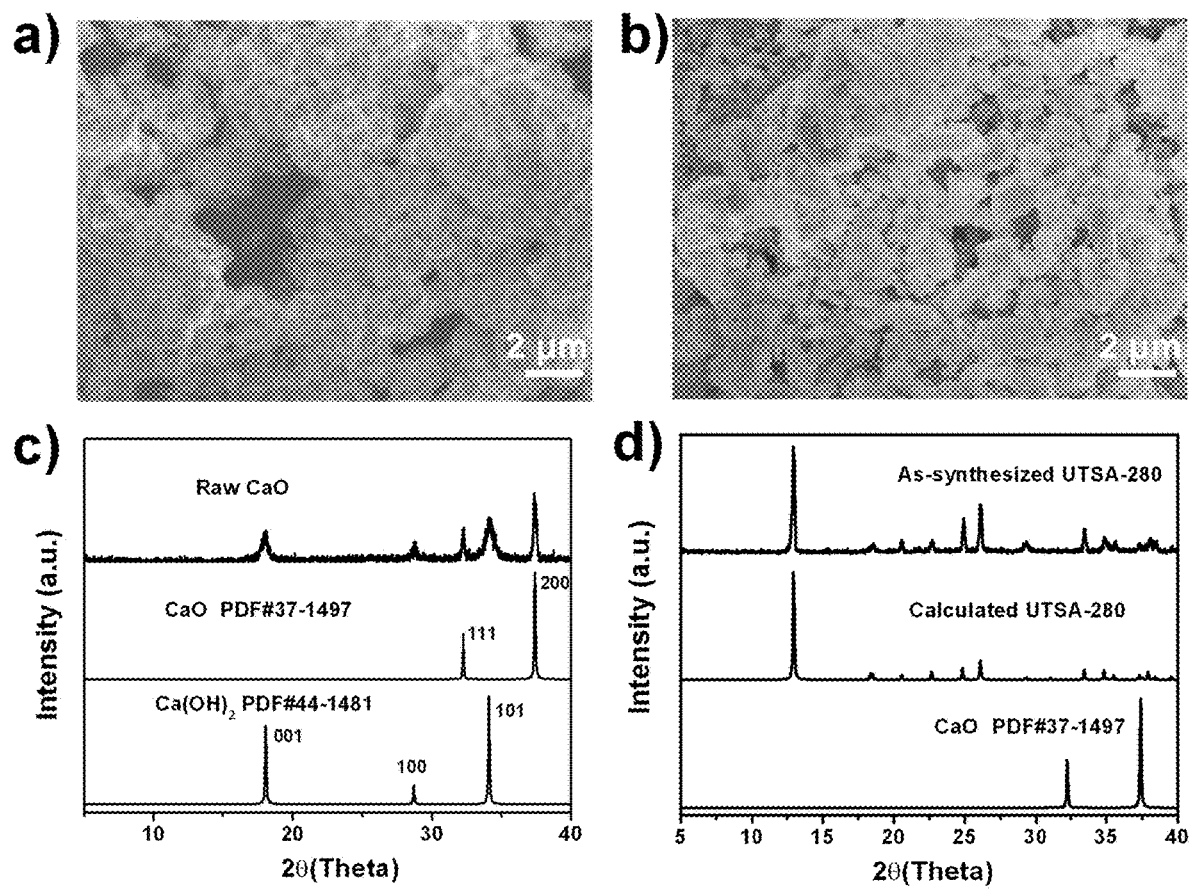
FIG. 3. SEM images and PXRD patterns of raw CaO(a,c) and as-synthesized UTSA-280 (b,d). The raw CaO was utilized as purchased. and it is sensitive to water, the extra peaks are attributed to reaction of CaO with water in the air.

Since $Ca(OH)_2$ is sensitive to carbon dioxide in the air (forming $CaCO_3$), the relatively stable CaO, which is the direct product from calcination of calcium carbonate, was then selected as an alternative calcium sources for preparation of UTSA-280. Interestingly, as shown in FIGS. 3 and 8, the reaction between CaO and squaric acid has been successfully conducted, giving pure UTSA-280. Again, CaO and the result UTSA-280 showed similar the morphologies with round and random shapes. And studies on different amounts of water were also conducted. The results also confirmed that no reaction happened without the presence of water; while the conversion from CaO and squaric acid to UTSA-280 increased with increasing amount of water, and a fully conversion from CaO and squaric acid to as-synthesized UTSA-280 was achieved at water molar ratio of 3 mol.

Figure 4:
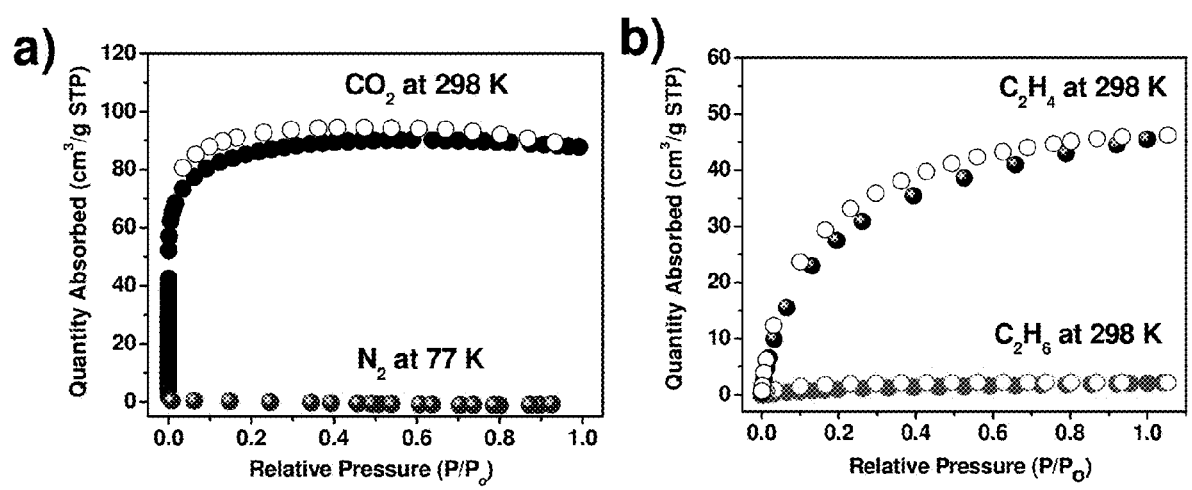
FIG. 4. Single-component gas sorption isotherms: a) carbon dioxide (black) at 195 K, nitrogen (blue) at 77 K and b) ethylene (black), ethane (red) at 298 K.
Figure 5:
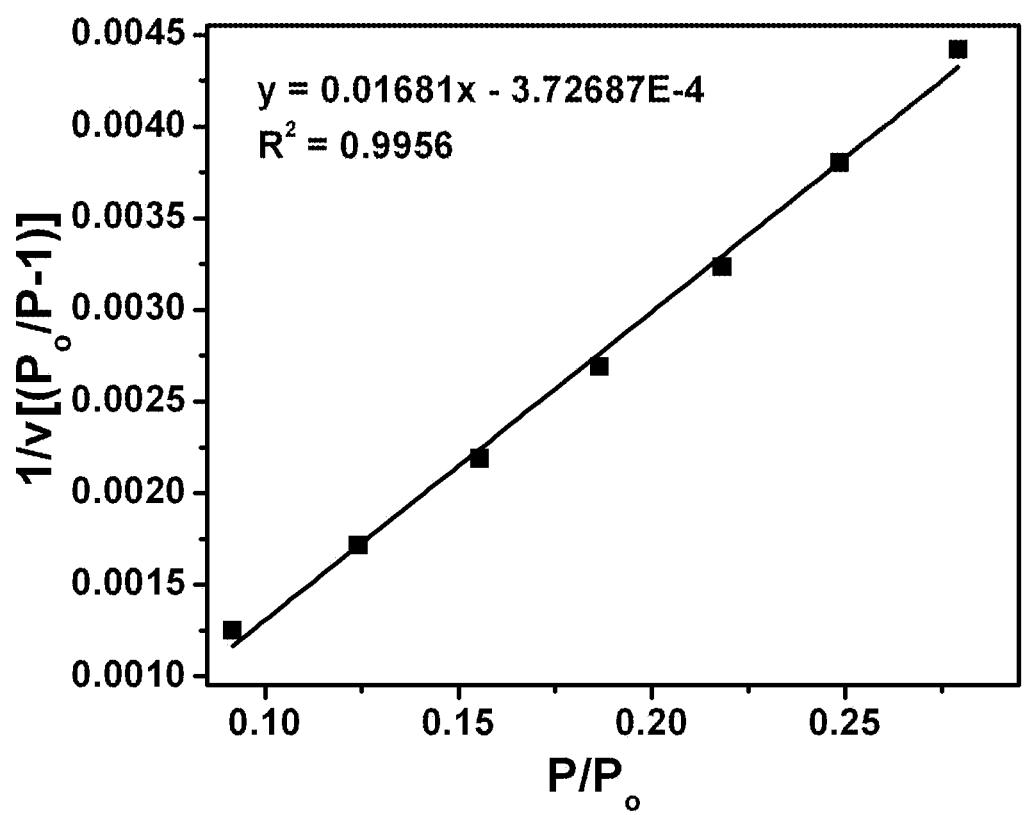
FIG. 5. Calculation of BET surface area for UTSA-280 based on $CO_2$ adsorption isotherm at 195 K.

The obtained UTSA-280 was further characterized with gas adsorption measurements to verify its selective adsorption performance. As shown in FIG. 4 and FIG. 5, the as-synthesized UTSA-280 exhibits no adsorption toward $N_2$ and high uptake to $CO_2$ (up to 84 cm$^3$/g), which is consistent with our previous results. The Brunauer-Emmett-Teller surface area of UTSA-280 was calculated to be 319 m$^2$/g, which is comparable with our previous result (331 m$^2$/g). See Mottillo et al., *Green Chemistry*, 19(12):2729-47, 2017, which is incorporated herein by reference in its entirety.

Activation was found in some embodiments to be important for the high sieving separation of ethylene/ethane. Specifically, insufficiently activation of the sample (not effectively remove the guest water molecules) or over activating (leading partial removal of the coordinated water) will both make UTSA-280 lose molecular sieving effects. Therefore, the activation of UTSA-280 should be carefully performed in some embodiments.

Considering the difference in particle size (0.3-3 µm) and shape (the previous one is 160 µm), activation conditions of current samples could be slightly varied. Since partial removal of coordinated water in UTSA-280 can result distortion or collapse of the framework structure, the varying particle sizes, temperatures, vacuum degrees should be taken into accounts. Different activation conditions have been applied to evaluate the sorption performance. When vacuuming the sample at 90° C. for 15 hours (under around $1 \times 10^{-5}$ bar, 8 µm Hg), there is only little amount uptake towards ethylene in the sample (FIG. 10). Further careful increase of the activation temperature to 103° C. for 15 hours (FIG. 11) with same vacuum degree, the sample exhibits high gas separation performance for ethylene over ethane, showing adsorption selectivity of more than >$10^3$ (FIGS. 6 and 9). Further increase of activation temperature to 115° C. for 15 hours, the partially decomposed UTSA-280 shows a significant increase of ethane uptake (up to 18 $cm^3/g$). In contrast, for sample of UTSA-280 from solution synthesis showing large particle size (160 µm), relatively harsh conditions are required (100-110° C., 24-48 h). See Lin et al., *Nat. Mater.*, 17(12):1128, 2018 and WO 2019/183635, both of which are incorporated by reference herein in their entireties.

Besides, the degree of vacuum should be carefully taken into consideration. Because, under ultra-high vacuum (e.g. <$1.0 \times 10^{-7}$ bar), the coordinated water in UTSA-280 can still be removed even at mild heating temperatures (FIGS. 12 and 13), indicating by additional peaks appeared in the diffraction patterns. Overall, the activation conditions are related to specific particle sizes, shapes and morphologies.

All of the compounds, material, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

WO 2019/183635
Aguado et al., *J. Am. Chem. Soc.*, 134:14635-14637, 2012.
Anderson, *Practical Process Research & Development—A Guide for Organic Chemists* (2012).
Anson et al., *Chem. Eng. Sci.*, 63:4171-4175, 2008.
Bachman et al. *J. Am. Chem. Soc.*, 139:15363-15370, 2017.
Bao et al., *Energy Environ. Sci.*, 9:3612-3641, 2016.
Bao et al., *Angew. Chem. Int. Ed.*, 130(49):16252-57, 2018.
Barone et al., *J. Comput. Chem.* 30, 934-939, 2009.
Bereciartua et al., *Science*, 358:1068-1071, 2017.
Bloch et al., *Science*, 335:1606-1610, 2012.
Cadiau et al., *Science*, 353:137-140, 2016.
Chang et al., *Chem. Commun.* 51:2859-2862, 2015.
Chu et al., *Nat. Mater.*, 16:16-22, 2017.
Crawford et al., *Chem. Sci.*, 6(3):1645-49, 2015.
Cui et al., *Science*, 353:141-144, 2016.
Cui et al., *Inorganica Chimica Acta*, 495:118938, 2019.
Faiz et al., *Chem. Eng. Sci.*, 73:261-284, 2012.
Friščić et al., *Angew. Chem. Int. Ed.*, 49(4):712-15, 2010.
Furukawa et al., *Science* 341(6149):1230444, 2013.
Geier et al., *Chem. Sci.* 4:2054-2061, 2013.
Giannozzi et al., *J. Phys.: Condens. Matter* 21:395502, 2009.
He et al., *Energy Environ. Sci.* 5:9107-9120, 2012.
Horike et al., *J. Am. Chem. Soc.*, 135:4612-4615, 2013.
Ji et al., *J. Am. Chem. Soc.*, 139:11325-11328, 2017.
Julien et al., *J. Am. Chem. Soc.*, 138(9):2929-32, 2016.
Kishida et al., *Angew. Chem. Int. Ed.* 55:13784-13788, 2016).
Kitagawa, *Angew. Chem. Int. Ed.*, 54:10686-10687, 2015.
Klet et al., *J. Am. Chem. Soc.* 137:15680-15683, 2015.
Krishna et al. *Microporous Mesoporous Mater.* 185:30-50, 2014.
Li et al., *Chem. Soc. Rev.*, 38(5):1477-1504, 2009.
Li et al., *J. Am. Chem. Soc.*, 136:8654-8660, 2014.
Li et al., *Chemistry—A European Journal*, 21(18):6913-20, 2015.
Li et al., *Science*, 362(6413):443-46, 2018.
Li et al., *Angew. Chem. Int. Ed.*, 130(46):15403-08, 2018.
Liao et al., *Science*, 356:1193-1196, 2017.
Lin et al., *Chem. Commun.*, 47(32):9185-87, 2011.
Lin, *Science*, 353:121-122, 2016.
Lin et al., *J. Am. Chem. Soc.*, 139(23):8022-28, 2017.
Lin et al., *Nat. Mater.*, 17(12):1128, 2018.
Lin et al., *J. Am. Chem. Soc.*, 140(40):12940-46, 2018.
Lin et al., *Coord. Chem. Rev.*, 378:87-103, 2019.
Lin et al., *Coord. Chem. Rev.*, 384:21-36, 2019.
Lin et al., *Chem*, 6(2):337-63, 2020.
Liu et al., *Chem. Soc. Rev.*, 47(12):4642-64, 2018.
Ma et al., *J. Am. Chem. Soc.*, 131:6445-6451, 2009.
Ma et al., *Science*, 361(6406):1008-11, 2018.
Majano et al., *Adv. Mater.*, 25(7):1052-57, 2013.
Maserati et al., *Chem. Mater.*, 28(5):1581-88, 2016.
Mofarahi et al., *Adsorption*, 19:101-110, 2013.
Mottillo et al., *Green Chemistry*, 19(12):2729-47, 2017.
Nugent et al., *Nature*, 495:80-84, 2013.
Pan et al., *Angew. Chem. Int. Ed.*, 45:616-619, 2006.
Peng et al., *Science*, 346:1356-1359, 2014.
Robl et al., *Mater. Res. Bull.*, 22:373-380, 1987.
Rubio-Martinez et al., *Chem. Soc. Rev.*, 46(11):3453-80, 2017.
Sen et al., *J. Am. Chem. Soc.*, 139:18313-18321, 2017.
Shi et al., *CrystEngComm*, 19(30):4265-68, 2017.
Sholl et al., *Nature*, 532:435-437, 2016.
Stojaković et al., *Chem. Commun.*, 48(64):7958-60, 2012.
Vaidhyanathan et al., *Science*, 330:650-653, 2010.
Webster et al., *J. Am. Chem. Soc.*, 120:5509-5516, 1998.
Yang et al., *Nat. Chem.* 7:121-129, 2014.
Yang, in *Adsorbents: Fundamentals and Applications*. (John Wiley & Sons, Inc.), pp. 280-381, 2003.
Yoon et al., *Angew. Chem. Int. Ed.*, 49:5949-5952, 2010.
Yoon et al., *Nat. Mater.*, 16:526-531, 2016.
Yuan et al., *Angew. Chem. Int. Ed.*, 49(23):3916-19, 2010.
Yuan et al., *CrystEngComm*, 12(12):4063-65, 2010.
Zhai et al., *Nat. Commun.*, 7:13645, 2016.
Zhao et al., *J. Am. Chem. Soc.*, 137(43):13756-59, 2015.
Zhang et al., *Chem. Commun.* 51:2714-2717, 2015.
Zhang, et al., *Energy & Fuels*, 22:1142-1147, 2008.
Zheng et al., *Inorg. Chem.*, 57:9096, 2018.

What is claimed is:

1. A method of preparing a metal organic framework (MOF) comprising a repeat unit of the formula:

[Ca(C$_4$O$_4$)(H$_2$O)]  (I)

or a hydrate thereof, comprising:
a) obtaining a first reagent, wherein the first reagent is CaO, Ca(OH)$_2$, or a combination thereof; and
b) admixing the first reagent with squaric acid under conditions suitable to form the MOF of formula I.

2. The method of claim 1, where the admixing comprises a mechanochemical process.

3. The method of claim 2, wherein the mechanochemical process comprises grinding the admixture of the first reagent and the squaric acid.

4. The method of claim 2, wherein the conditions comprise the presence of water.

5. The method of claim 4, wherein the molar ratio of the water to the first reagent is from about 1:1 to about 10:1.

6. The method of claim 5, wherein the molar ratio is about 5:1.

7. The method of claim 1, wherein the admixing step is conducted in the absence of any organic solvents.

8. The method of claim 1, wherein the method does not generate any stoichiometric quantities of salt byproducts.

9. The method of claim 1, wherein the admixing is conducted at a temperature from about 0° C. to about 30° C.

10. The method of claim 1, wherein the first reagent is CaO.

11. The method of claim 10, wherein the molar ratio of CaO to squaric acid is about 1:1.

12. The method of claim 1, wherein the first reagent is Ca(OH)$_2$.

13. The method of claim 1, wherein the C$_4$O$_4^{2-}$ group is of the formula:

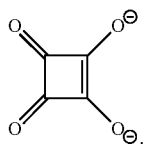

(A)

14. The method of claim 1, further comprising washing the MOF after the admixing step.

15. The method of claim 1, further comprising activating the MOF.

16. The method of claim 15, wherein the MOF is activated by heating the MOF at a temperature from about 50° C. to about 300° C.

17. The method of claim 1, wherein more than one kilogram of the MOF is prepared.

18. A metal organic framework (MOF) prepared by the method according to claim 1.

19. A method of separating two or more compounds using a metal organic framework (MOF) prepared by mechanochemical synthesis, wherein the MOF comprises a repeating unit of the formula ML, wherein M is a divalent metal ion and L is a ligand of the formula:

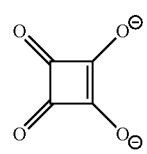

(A)

or a hydrate thereof, wherein the method comprises:
(A) combining the metal-organic framework with a mixture comprising a first compound and a second compound, wherein the first compound and the second compound are different types of gases; and
(B) separating the first compound from the second compound within the metal-organic framework.

20. The method of claim 19, wherein M is Ca(II).

* * * * *